(12) United States Patent
Abudawoud

(10) Patent No.: US 9,000,247 B2
(45) Date of Patent: Apr. 7, 2015

(54) COMBINED HEAVY REFORMATE DEALKYLATION-TRANSALKYLATION PROCESS FOR MAXIMIZING XYLENES PRODUCTION

(71) Applicant: Saudi Arabian Oil Company, Dhahran (SA)

(72) Inventor: Raed Abudawoud, Khobar (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 13/866,559

(22) Filed: Apr. 19, 2013

(65) Prior Publication Data

US 2013/0281750 A1     Oct. 24, 2013

Related U.S. Application Data

(60) Provisional application No. 61/635,412, filed on Apr. 19, 2012.

(51) Int. Cl.
    *C07C 6/12*         (2006.01)
    *C07C 4/14*         (2006.01)
             (Continued)

(52) U.S. Cl.
    CPC ... *C07C 4/18* (2013.01); *C07C 6/06* (2013.01); *C07C 6/126* (2013.01); *C07C 6/123* (2013.01)

(58) Field of Classification Search
    CPC .......... C07C 6/123; C07C 6/126; C07C 4/20; C07C 15/02; C07C 15/06; C07C 15/08
    USPC .......................... 585/319, 488, 489, 470, 475
    See application file for complete search history.

(56) References Cited

U.S. PATENT DOCUMENTS 4,127,471 A    11/1978   Suggitt et al.
5,030,787 A    7/1991    Absil et al.
(Continued)

FOREIGN PATENT DOCUMENTS

EP        0816311 A1     1/1998

OTHER PUBLICATIONS

PCT Notification of Transmittal of the International Search Report and the Written Opinion of the International Searching Authority, or the Declaration; dated Jul. 4, 2013; International Application No. PCT/US2013/037304; International File Date: Apr. 19, 2013.

(Continued)

*Primary Examiner* — Thuan D Dang
(74) *Attorney, Agent, or Firm* — Bracewell & Giuliani LLP; Constance Gall Rhebergen

(57) ABSTRACT

A method of forming mixed xylenes from a heavy reformate using a dealkylation-transalkylation system includes the step of introducing both a heavy reformate containing methyl ethyl benzenes and tri-methyl benzenes and that is sufficiently free of toluene and a hydrogen-containing material into the dealkylation stage such that the heavy reformate and the hydrogen-containing material intermingle and contact the hydrodealkylation catalyst. The dealkylation-transalkylation system includes dealkylation, non-aromatic product gas separations and transalkylation stages. Toluene forms from the reaction of methyl ethyl benzenes and hydrogen in the presence of the hydrodealkylation catalyst. The method also includes the step of introducing a dealkylated heavy reformate into the transalkylation stage such that the dealkylated heavy reformate contacts a transalkylation catalyst, forming a transalkylation stage product mixture includes mixed xylenes.

13 Claims, 2 Drawing Sheets

(51) Int. Cl.
*C07C 4/18* (2006.01)
*C07C 6/06* (2006.01)

(56) References Cited

U.S. PATENT DOCUMENTS

| | | | |
|---|---|---|---|
| 5,763,720 | A | 6/1998 | Buchanan et al. |
| 5,847,256 | A | 12/1998 | Ichioka et al. |
| 5,866,741 | A | 2/1999 | Wu et al. |
| 5,942,651 | A | 8/1999 | Beech, Jr. et al. |
| 5,952,536 | A | 9/1999 | Nacamuli et al. |
| 6,096,938 | A | 8/2000 | Ghosh |
| 6,359,184 | B1 | 3/2002 | Kato et al. |
| 7,544,849 | B2 | 6/2009 | Boldingh et al. |
| 7,563,358 | B2 | 7/2009 | Stavens et al. |
| 7,663,010 | B2 | 2/2010 | Levin |
| 8,071,828 | B2 | 12/2011 | Cao et al. |
| 8,183,424 | B2 | 5/2012 | Levin et al. |
| 8,198,502 | B2 | 6/2012 | Bresler et al. |
| 2005/0197518 | A1 | 9/2005 | Miller et al. |
| 2008/0021253 | A1 | 1/2008 | Corma Canos et al. |
| 2009/0112034 | A1 | 4/2009 | Levin |
| 2012/0024755 | A1 | 2/2012 | Beech, Jr. et al. |
| 2012/0083638 | A1 | 4/2012 | Boldingh et al. |

OTHER PUBLICATIONS

James A. Johnson, "Aromatics Complexes", Handbook of Petroleum Refining Processes Third Edition, 2004, pp. 2.3-2.11, McGraw Hill, USA.

Patrick J. Silady, "UOP Isomar Process", Handbook of Petroleum Refining Processes Third Edition, 2004, pp. 2.39-2.46, McGraw Hill, USA.

Scott E. Commissaris, "UOP Parex Process", Handbook of Petroleum Refining Processes Third Edition, 2004, pp. 2.47-2.54, McGraw Hill, USA.

Negiz and Stoodt, "UOP Tatoray Process", Handbook of Petroleum Refining Processes Third Edition, 2004, pp. 2.55-2.63, McGraw Hill, USA.

COMBINED HEAVY REFORMATE DEALKYLATION-TRANSALKYLATION PROCESS FOR MAXIMIZING XYLENES PRODUCTION

CROSS-REFERENCE TO RELATED PATENT APPLICATIONS

This application claims priority from U.S. Provisional Application No. 61/635,412, filed Apr. 19, 2012. For purposes of United States patent practice, this application incorporates the contents of the Provisional Application by reference in its entirety.

BACKGROUND OF THE INVENTION

1. Field of the Invention

The field of invention relates to the production of mixed xylenes. More specifically, the field relates to the production of mixed xylenes using heavy reformate.

2. Description of the Related Art

Petrochemical refiners are facing issues with the utilization of heavy reformate streams. Environmental regulations are limiting the amount of aromatics (C6+) content in gasoline fuel. Gasoline refiners and blenders traditionally use C6+ aromatics, which include the C6-8 BTEX components (Benzene, Toluene, Ethylbenzene and mixed Xylenes) to improve octane ratings and anti-knocking attributes of motor fuels.

Although motor fuel use is a major consumer of BTEX components, each of the BTEX products has alternative markets for their use besides motor fuels. Benzene is a widely used precursor for many chemical and solvation processes. Toluene and ethylbenzene are also reactants and precursors in chemical and polymerization processes. The three isomers of xylene ($C_8H_{10}$)—para-xylene (p-xylene), meta-xylene (m-xylene) and ortho-xylene (o-xylene)—are all petrochemical feedstocks of value.

"Mixed xylenes" is a mixture of all three xylene isomers. P-xylene is a feed for polyester, a polymer with significant and growing global demand. O-xylene is the feedstock for phthalic anhydride manufacturing, which, in turn, feeds alkyd resin and urethane production. M-xylene has a lower commercial demand than the other two xylenes and makes isophthalic acid and plasticizers. When mixed xylenes form during catalytic reformation, meta-xylene forms in greater amounts than para-xylene and ortho-xylene because of thermodynamics. Market demand, however, currently favors p-xylene followed distantly by o-xylene.

Reformate, which is the bottoms product from naphtha catalytic reforming, and pyrolysis gasoline ("pygas"), a byproduct of ethylene cracking, are the usual sources for these compounds. Extracting the BTEX components from reformate and pygas leaves a heavy reformate, which comprises mainly C9+ alkyl aromatic compounds (pygas may also contain diolefins). Heavy reformate can also form from running hydrogen production process at a greater severity (that is, temperature) to produce additional hydrogen alkanes and olefins from the same naphtha feedstock.

The heavy reformate as a chemical stream in and of itself has little direct commercial value. Any ability to blend away C9+ alkyl aromatics into gasoline pools is shrinking rapidly.

Toluene is not usually found in heavy reformate as it has been previously recovered or the heavy reformate forms under severe processing conditions such that light aromatics like toluene do not form. Often petrochemical refiners that use transalkylation to convert tri-methyl benzenes found in heavy reformate into xylenes add previously extracted toluene back into the heavy reformate stream. This is a waste of processing energy and unnecessarily increases capital expenditure.

SUMMARY OF THE INVENTION

A dealkylation-transalkylation system that is useful for forming mixed xylenes from a heavy reformate that includes both methyl ethyl benzenes and tri-methyl benzenes includes a dealkylation stage, a non-aromatic product gas separations stage and a transalkylation stage. The dealkylation stage contains a hydrodealkylation catalyst. The hydrodealkylation catalyst is operable to selectively convert methyl ethyl benzenes and hydrogen into toluene and a non-aromatic product gas. The dealkylation stage is operable to receive both a hydrogen-containing material and the heavy reformate, and it is operable to also produce a dealkylation stage product that contains toluene, tri-methyl benzenes and non-aromatic product gas. The non-aromatic product gas separations stage is fluidly coupled to the dealkylation stage. The non-aromatic product gas separations stage is operable to receive the dealkylation stage product, and it is operable to produce separately the non-aromatic product gas and a dealkylation heavy reformate that contains toluene and tri-methyl benzenes. The transalkylation stage is fluidly coupled to the non-aromatic product gas separations stage and contains a transalkylation catalyst. The transalkylation catalyst is operable to selectively convert tri-methyl benzenes and toluene into mixed xylenes. The hydrodealkylation catalyst and the transalkylation catalyst are not the same material. The transalkylation stage is operable to receive the dealkylation heavy reformate, and it is operable to produce a transalkylation stage product that contains mixed xylenes. The hydrodealkylation catalyst and the transalkylation catalyst are not contained in the same stage.

A method of forming mixed xylenes from a heavy reformate using the dealkylation-transalkylation system includes the step of introducing both the heavy reformate and a hydrogen-containing material into the dealkylation stage of the dealkylation-transalkylation system such that the heavy reformate and the hydrogen-containing material intermingle and contact the hydrodealkylation catalyst. The introduced heavy reformate includes a significant amount of both methyl ethyl benzenes and tri-methyl benzenes and is substantially free of toluene by weight. The introduced hydrogen-containing material includes hydrogen. The method also includes the step of operating the dealkylation stage such that both toluene forms from the reaction of methyl ethyl benzenes and hydrogen in the presence of the hydrodealkylation catalyst and a dealkylation stage product is produced. The dealkylation stage product includes toluene, tri-methyl benzenes and non-aromatic product gas. The method also includes operating the non-aromatic product gas separations stage such that the non-aromatic product gas and a dealkylation heavy reformate are produced separately. The dealkylation heavy reformate comprises toluene and tri-methyl benzenes. The method also includes the step of introducing the dealkylated heavy reformate into the transalkylation stage such that the dealkylated heavy reformate contacts a transalkylation catalyst. The method also includes the step of operating the transalkylation stage such that both mixed xylenes form from the reaction of tri-methyl benzenes and toluene in the presence of the transalkylation catalyst and a transalkylation stage product is produced. The transalkylation stage product mixture includes mixed xylenes.

A way to produce mixed xylenes and other BTEX components from a heavy reformate containing C9+ aromatics uses transalkylation to react tri-methyl benzenes ("TMBs"), which are C9 alkyl aromatics found in heavy reformate, with toluene in the presence of a transalkylation-selective catalyst to form mixed xylenes.

In the method, toluene is formed in-situ as the heavy reformate is processed before transalkylation. A preceding dealkylation process using a hydrodealkylation catalyst and hydrogen selectively converts methyl ethyl benzenes ("MEBs") introduced with the heavy reformate into toluene and ethane. A downstream non-aromatic product gas separations process removes the alkane product gases and unreacted hydrogen from the dealkylated aromatics before transalkylation.

The method calls for converting the heavy reformate in two separate stages (reactors in series). In the dealkylation stage, a selective dealkylation catalyst maximizes the in-situ toluene production by selective hydrodealkylation of the MEBs. In the transalkylation stage, the selective transalkylation catalyst processes the resultant of the dealkylation stage after degassing. Toluene in the dealkylated heavy reformate transalkylates the TMBs, which are unconverted in the dealkylation stage, into mixed xylenes in the transalkylation stage. The system operates such that p-xylene preferably forms by appropriate section of the transalkylation catalyst and management of operating conditions of the transalkylation stage.

Useful amounts of benzene, toluene, alkanes and olefins, which are all commercially valuable, form during the dealkylation-transalkylation process. In a variety of embodiments to the method, at least some of the benzene, toluene, mixed xylenes and m-xylene are recycled to alter the thermodynamics of the transalkylation process and enhance the production of p-xylene.

The dealkylation-transalkylation method enables the maximization of xylenes from low-value heavy reformates (C9+). Using the dealkylation-transalkylation two-stage reaction system, the dealkylation stage maximizes the dealkylation of the MEBs in the heavy reformate for in-situ generation of toluene and the downstream transalkylation stage selectively transalkylates the TMBs with the in-situ generated toluene. This separate and distinct two-part reaction system improves the yield of the mixed xylenes for the heavy reformate material over a single stage or vessel system. A single catalyst that is optimally selective for dealkylation at a particular set of operating conditions is not also optimally selective for transalkylation at the same operating conditions, and vice versa. Different catalyst and operating conditions improve efficiency and selectivity. Using a dual-catalyst system in a single-stage or vessel system can cause C9+ alkyl aromatics such as TMBs to disproportionate or transalkylate into heavier alkyl aromatics. Such side-reactions can cause rapid catalyst deactivation via coking and the formation of polyaromatics.

The dealkylation-transalkylation method removes light, non-aromatic product gases from the dealkylation stage product before it is introduced into the vessel where transalkylation occurs. This degassing reduces the physical size of the vessel required for the transalkylation stage. The removal of the non-aromatic gases also improves the efficiency of the transalkylation process by removing diluent materials. In single-stage systems using a dual-catalyst system, light gases that form during the dealkylation process cause an increase in the volume of the catalyst bed as entrained gases attempt to escape the catalyst bed.

The dealkylation-transalkylation method does not require the introduction or recycle of benzene, toluene, mixed xylenes, meta-xylene or any other aromatic streams into the system beyond the treated heavy reformate. Since the dealkylation stage generates toluene in-situ, the introduction of virgin aromatics to assist in the conversion of C9+ alkyl aromatics is not required. Such materials can be optionally recycled from downstream refining process to form desired system products at desired ratios to one another.

The method of using the dealkylation-transalkylation, using a low-value heavy reformate stream and a little hydrogen, can produce a spectrum of useful and commercially valuable chemicals that greatly improves the economics for a petrochemical processor. The in-situ generation of toluene as part of the process not only consumes MEBs and converts them to useful components but also eliminates the requirement for using prior-processed BTEX chemicals for effecting the conversion of TMBs. Optionally, at least a portion of the benzene, toluene, or one or more isomers of xylenes, including mixed xylene and meta-xylene, can be recycled and reintroduced into the transalkylation stage or the dealkylation stage to change the intermediate and final product mixtures. The conversion of MEBs into toluene in situ provides sufficient toluene for conversion of the remaining TMBs into mixed xylenes.

BRIEF DESCRIPTION OF THE DRAWINGS

These and other features, aspects, and advantage of the present invention will be better understood with regard to the following Detailed Description, appended Claims, and accompanying Figures, where:

Figure 1:
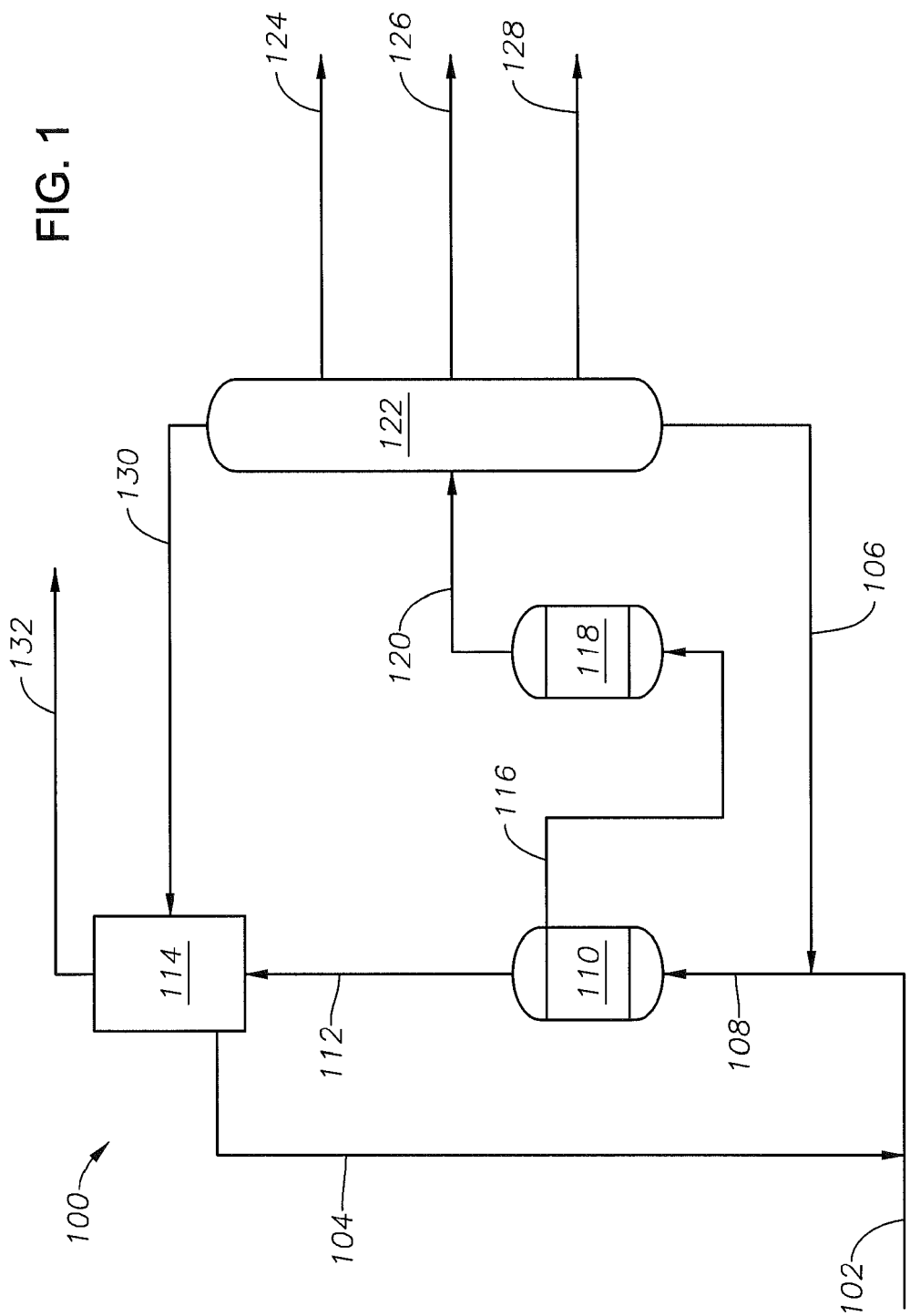
FIG. 1 is a process flow diagram for an embodiment of the dealkylation-transalkylation system.

In the accompanying Figures, a similar component or feature, or both, may have a similar reference label.

The Figures are general process flow diagrams of an embodiment of the dealkylation-transalkylation system. The Figures and its description facilitate a better understanding of the dealkylation-transalkylation system and its method of use. In no way should the Figures limit or define the scope of the invention. The Figures are a simple diagram for ease of description. Those of ordinary skill in the art understand that such systems are complex structures with ancillary equipment and subsystems that render them operable for their intended purpose.

DETAILED DESCRIPTION OF THE PREFERRED EMBODIMENTS

The Specification, which includes the Summary of Invention, Brief Description of the Drawings and the Detailed Description of the Preferred Embodiments, and the appended Claims refer to particular features (including process or method steps) of the invention. Those of skill in the art understand that the invention includes all possible combinations and uses of particular features described in the Specification. Those of skill in the art understand that the invention is not limited to or by the description of embodiments given in the Specification. The inventive subject matter is not restricted except only in the spirit of the Specification and appended Claims.

Those of skill in the art also understand that the terminology used for describing particular embodiments does not limit the scope or breadth of the invention. In interpreting the Specification and appended Claims, all terms should be interpreted in the broadest possible manner consistent with the context of each term. All technical and scientific terms used in the Specification and appended Claims have the same meaning as commonly understood by one of ordinary skill in the art to which this invention belongs unless defined otherwise.

As used in the Specification and appended Claims, the singular forms "a", "an", and "the" include plural references unless the context clearly indicates otherwise. The verb "comprises" and its conjugated forms should be interpreted as referring to elements, components or steps in a non-exclusive manner. The referenced elements, components or steps may be present, utilized or combined with other elements, components or steps not expressly referenced. The verb "couple" and its conjugated forms means to complete any type of required junction, including electrical, mechanical or fluid, to form a singular object from two or more previously non-joined objects. If a first device couples to a second device, the connection can occur either directly or through a common connector. "Optionally" and its various forms means that the subsequently described event or circumstance may or may not occur. The description includes instances where the event or circumstance occurs and instances where it does not occur. "Operable" and its various forms means fit for its proper functioning and able to be used for its intended use. "Associated" and its various forms means something connected with something else because they occur together or that one produces the other.

Spatial terms describe the relative position of an object or a group of objects relative to another object or group of objects. The spatial relationships apply along vertical and horizontal axes. Orientation and relational words including "upstream" and "downstream" and other like terms are for descriptive convenience and are not limiting unless otherwise indicated.

Where the Specification or the appended Claims provide a range of values, it is understood that the interval encompasses each intervening value between the upper limit and the lower limit as well as the upper limit and the lower limit The invention encompasses and bounds smaller ranges of the interval subject to any specific exclusion provided. "Substantially free" means less than 1% by the indicated unit of measure. "Significant" means equal to or greater than 10% by the indicated unit of measure. "Detectable amount" means 0.1% by the indicated unit of measure.

Where the Specification and appended Claims reference a method comprising two or more defined steps, the defined steps can be carried out in any order or simultaneously except where the context excludes that possibility.

When a patent or a publication is referenced in this disclosure, the reference is incorporated by reference and in its entirety to the extent that it does not contradict statements made in this disclosure.

FIG. 1

FIG. 1 is a process flow diagram for an embodiment of the dealkylation-transalkylation system. Process 100 begins with the introduction of C9+ heavy reformate feed stream 102. Feed stream 102 contains alkyl aromatics of the C9 and C10 variety and is vaporized. Feed stream 102 combines with hydrogen recycle stream 104 and heavy aromatics recycle stream 106, forming a combined feed stream 108. Process 100 passes combined feed stream 108 into dealkylation reactor 110.

A catalytic hydrodealkylation reaction in dealkylation reactor 110 removes the alkyl groups ethyl and higher from their associated aromatic rings. The conversion of the feed results in the formation of light alkanes, which includes ethane, and olefins, which includes propylene. In addition, some unused hydrogen passes from dealkylation reactor 110. The light, non-aromatic gases separate from the aromatics and move through dealkylator lights stream 112 to gas processing system 114. The dealkylation aromatics, which include benzene, toluene and other methylated aromatics, pass from dealkylation reactor 110 through dealkylation reactor product stream 116.

Dealkylation reactor product stream 116 introduces the dealkylated heavy reformate into transalkylation reactor 118. Transalkylation reactor 118 promotes the reaction of benzene and toluene with the tri-methylated aromatics to form mixed xylenes and toluene. Disproportionation of methylated aromatics also creates additional mixed xylenes and C10 alkyl aromatics. The xylene-rich product stream passes from transalkylation reactor 118 through xylene splitter feed stream 120.

Aromatics splitter feed stream 120 introduces the xylene-rich product stream to aromatics splitter 122. Aromatics splitter 122 selectively separates and passes product streams of benzene 124, toluene 126 and mixed xylenes 128. Aromatics splitter lights stream 130 passes alkanes and olefins formed in transalkylation reactor 118 to gas processing system 114 for separation. Process 100 recycles heavier-than-xylene (C9+) alkyl aromatics, which include C10 alkyl aromatics formed in transalkylation reactor 118, through heavy aromatics recycle stream 106.

Gas processing system 114 receives the contents of dealkylator lights stream 112 and aromatics splitter lights stream 130 and separates the hydrogen from the alkanes and olefins. Hydrogen recycle stream 104 conveys hydrogen passing from gas processing system 114 to the upstream portion of process 100 for use in dealkylation reactor 110 as a hydrogen-containing material. Light chemicals stream 132 transports the alkanes and the olefins to processes outside of process 100.

FIG. 2

Figure 2:
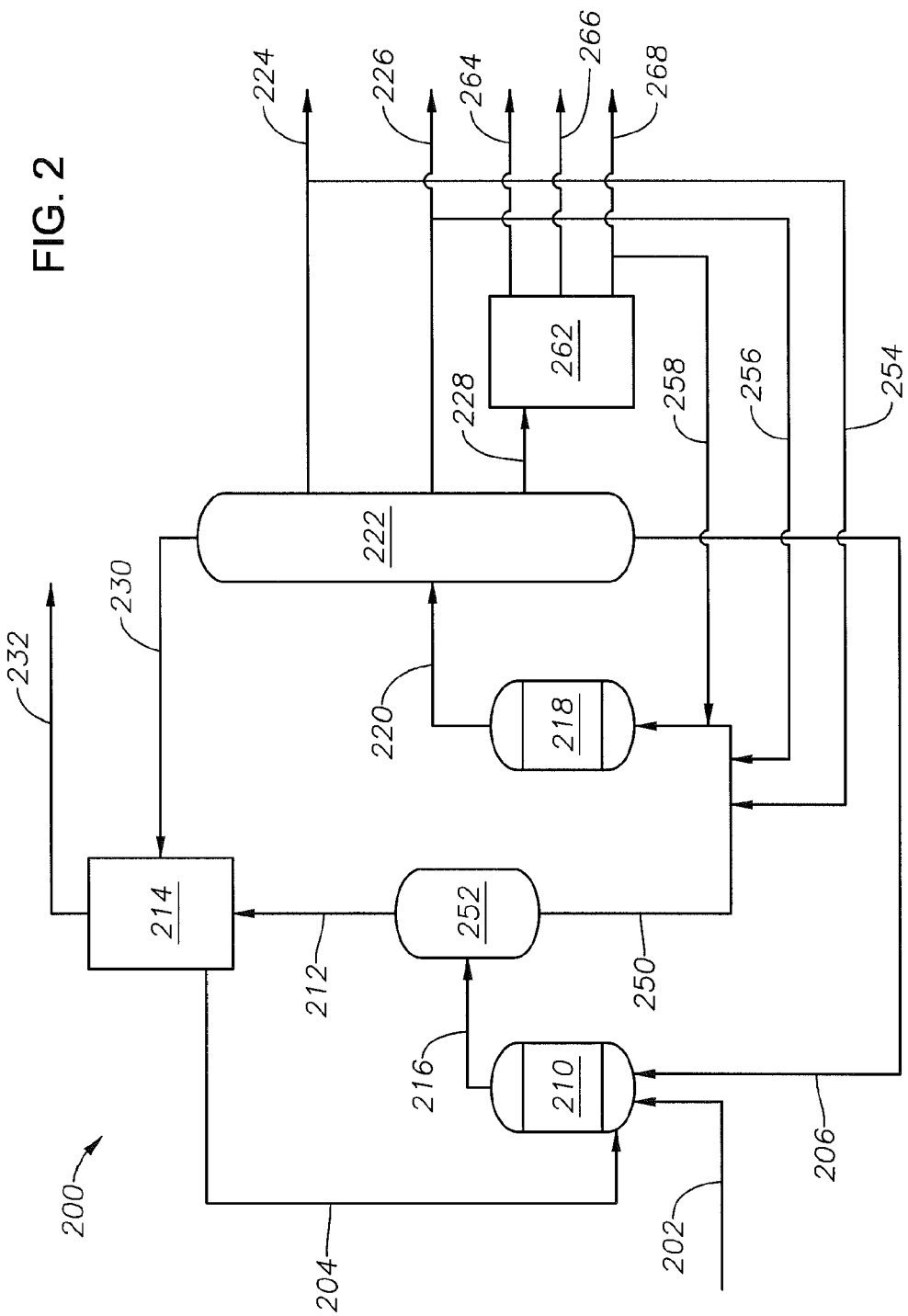
FIG. 2 is a process flow diagram for an embodiment of the dealkylation-transalkylation system that includes additional recycling and separations processes.

FIG. 2 is a process flow diagram for an embodiment of the dealkylation-transalkylation system that includes additional recycling and separations processes. Process 200 takes advantage of additional recycling and separations process to maximize xylene production. Process 200 begins with the introduction of C9+ heavy reformate feed stream 202. Feed stream 202 contains C9+ alkyl aromatics. Feed stream 202, hydrogen recycle stream 204 and heavy aromatics recycle stream 206 each pass into dealkylation reactor 110 separately.

The catalytic hydrodealkylation reaction in dealkylation reactor 210 removes alkyl groups higher than ethyl from their associated aromatic rings. A mixed dealkylated heavy reformate and light, non-aromatic gases passes from dealkylation reactor 210 through dealkylation reactor product stream 216.

Dealkylation reactor product stream 216 introduces the mixed dealkylated heavy reformate and light, non-aromatic gases into non-aromatic gas separator 252. Non-aromatic gas separator 252 separates the non-aromatic gases, which includes hydrogen, from the dealkylated heavy reformate. Process 200 directs the light, non-aromatic gases from non-aromatic gas separator 252 through dealkylator lights stream 212 into gas processing system 214. Process 200 also directs the dealkylated heavy reformate from non-aromatic gas separator 252 through transalkylation reactor feed stream 250 toward transalkylation reactor 218.

Before introduction into transalkylation reactor 218, optionally, at least a portion of the produced benzene is introduced through benzene recycle stream 254, at least a portion of the produced toluene is introduced through toluene recycle stream 256 and at least a portion of the produced meta-xylene is introduced through m-xylene recycle stream 258. FIG. 2 shows the optional ability to supplement the dealkylated heavy reformate with at least some, if not all, of the production amounts of m-xylene, toluene and benzene, forming a supplemented dealkylated heavy reformate. The elective supplementation increases the ratio of C6-8s in the transalkylation reactor feed stream 250 to alter the reaction output of transalkylation reactor 218 and facilitate p- and o-xylene production.

Transalkylation reactor feed stream 250 introduces the supplemented dealkylated heavy reformate into transalkylation reactor 218. Transalkylation reactor 218 facilitates the benzene and toluene reaction with the methylated aromatics to form mixed xylenes and toluene. The xylene-rich product stream passes from transalkylation reactor 218 through splitter feed stream 220.

Splitter feed stream 220 introduces the xylene-rich product stream to aromatics splitter 222. Aromatics splitter 222 separates and produces product streams of benzene 224, toluene 226 and mixed xylenes 228. Process 200 is operable to recycle both at least a portion, if not all, of the produced benzene through benzene recycle stream 254 and at least a portion, if not all, of the toluene through toluene recycle stream 256 to upstream portions of process 200. Aromatics splitter 222 passes the mixed xylenes through mixed xylenes product stream 228 to xylene separations 262 for additional processing. Aromatics splitter lights stream 230 passes light alkanes and olefins to gas processing system 214 for further separation. Heavier-than-xylene (C9+) alkyl aromatics are recycled in process 200 through heavy aromatics recycle stream 206.

Xylene separations 262 selectively separates and produces product streams of p-xylene 264, o-xylene 266 and m-xylene 268 from the introduced mixed xylenes stream. Process 200 is operable to recycle at least a portion, if not all, of the produced m-xylene through m-xylene recycle stream 258 to upstream portions of process 200.

Gas processing system 214 receives dealkylator lights stream 212 and aromatic splitter lights stream 130 and separates the alkanes and the olefins from the hydrogen. Hydrogen recycle stream 204 passes hydrogen from gas processing system 214 to dealkylation reactor 210. Light chemicals stream 232 transports the alkanes and olefins away from process 200.

Process Reactants

The introduced reactant materials for the method of dealkylation-transalkylation are heavy reformate, which contains C9+ alkyl aromatics, and hydrogen-containing material, which contains hydrogen.

The hydrocarbon feed for the dealkylation-transalkylation is a "heavy" reformate. Modern catalytic reforming processes and ethylene crackers operate to maximize light gas and hydrogen production by catalytically reforming naphtha feed stocks. In turn, aromatics and alkyl aromatics concentrate in the bottoms or tails streams of these process to form a reformate. Recovery of light aromatics from the reformate or a great enough severity in reforming naphtha produces a "heavy" reformate. The heavy reformate can originate from sources internal to or external of the processing facility. One source is from a bottoms or tails stream after reforming naphtha and extracting the BTEX compounds. This heavy reformate has a typical composition of C9+ alkyl aromatics and is sufficiently free of C6-8s. The heavy reformate can be what is considered straight reformate, which contains C6+ aromatics and alkyl aromatics. Heavy fractionation of pyrolysis gasoline or liquids coal materials from coking operations can supply "heavy" reformate. The dealkylation-transalkylation process itself can also provide a recycle stream containing unreacted C9+ alkyl aromatics. One of ordinary skill in the art can clearly recognize other sources of C9+ alkyl aromatics that are useful for the dealkylation-transalkylation process.

Regardless of the source, useful heavy reformate comprises MEBs suitable for conversion into toluene and TMBs suitable for conversion into mixed xylenes. Useful heavy reformate comprises MEBs in a range of from about 15 wt. % to about 50 wt. % and TMBs in a range of from about 25 wt. % to about 80 wt. %. The weight ratio value of MEBs to TMBs in heavy reformate compositions can be from about 0.01 to about 100. An embodiment of the method includes where the weight ratio value of MEBs to TMBs in the heavy reformate is in a range of from about 0.1 to about 3. Other components are optionally present in the useful heavy reformate, including other C9 aromatics, including isopropylbenzene, which are present in a range of from 0 wt. % to about 15 wt. %, C10 aromatics, which are present in a range of from 0 wt. % to about 25 wt. %, C11 aromatics, which are present in a range of from 0 to about 5 wt. %, and a combination of mixed xylenes and ethylbenzene, which are present as a combination in a range of from 0 to about 5 wt. %. Useful heavy reformates are optionally substantially free of any of the other C9 aromatics, C10 aromatics, C11 aromatics, mixed xylenes and ethylbenzenes, and combinations thereof. Useful heavy reformates may contain less than detectable amounts of any of the other C9 aromatics, C10 aromatics, C11 aromatics, mixed xylenes and ethylbenzenes, and combinations thereof.

An embodiment of the method includes introducing the heavy reformate that is substantially free of all of the individual BTEX compounds. The heavy reformate has been previously processed in a BTEX recovery unit before passing to the dealkylation-transalkylation system. An embodiment of the method includes introducing the heavy reformate having less than detectable amounts of the individual BTEX compounds.

Table 1 shows an example assay of a heavy reformate stream produced from a naphtha reformer system.

TABLE 1

Example assay of a useful heavy reformate.

| Major Compound | Abbreviation | Composition, wt % |
|---|---|---|
| Iso-propyl benzene | iPB | 1.7 |
| n-propyl benzene | nPB | 4.3 |
| 1-methyl 2-ethyl benzene | 1M2EB | 6.5 |
| 1-methyl 3-ethyl benzene | 1M3EB | 18.5 |
| 1-methyl 4-ethyl benzene | 1M4EB | 9.1 |
| 1,2,3-tri-methyl benzene | 123TMB | 6.6 |
| 1,2,4-tri-methyl benzene | 124TMB | 39.0 |
| 1,3,5-tri-methyl benzene | 135TMB | 10.1 |
| Total C9 aromatics | | 95.9 |
| n-butyl benzene | nBB | 0.5 |
| 1,4-diethyl benzene | 14DEB | 0.8 |
| 1,3-diethyl benzene | 13DEB | 0.4 |
| 1,3-dimethyl, 5-ethyl benzene | 13DM5EB | 0.8 |
| 1,4-dimethyl, 2-ethyl benzene | 14DM2EB | 0.4 |
| Others C10s | | 1.2 |
| Total C10 aromatics | | 4.1 |

The total amount of methyl ethyl benzenes in the heavy reformate composition of Table 1 is approximately 34.1 weight percent. An embodiment of the method of forming mixed xylenes from a heavy reformate includes introducing heavy reformate having methyl ethyl benzenes comprises at least about 30 percent by weight. The cumulative amount of tri-methyl benzenes ("TMBs") in the same heavy reformate composition is approximately 55.7 weight percent. An embodiment of the method includes introducing heavy reformate having a greater amount of TMBs than MEBs by weight. The weight ratio value of MEBs to TMBs for the heavy reformate composition in Table 1 is about 0.61.

The heavy reformate of Table 1 is substantially free of toluene. An embodiment of the method of forming mixed xylenes from a heavy reformate includes introducing heavy reformate that is substantially free of toluene. An embodiment of the method of forming mixed xylenes from a heavy reformate includes introducing heavy reformate that comprises less than a detectable amount of toluene by weight. MEBs are the toluene precursor for the method. Toluene formed in-situ from the MEBs transalkylates with the TMBs.

The introduced hydrogen-containing material contains hydrogen. The hydrogen supplied to the dealkylation stage through the hydrogen-containing material can originate from various sources. The hydrogen can originate from liquefied or cryogenic storage facilities, which vaporizes the high-pressure liquid hydrogen for use. The hydrogen-containing material can come from other process units as a product or recycle gas stream, including hydrocracking systems. Other portions of the dealkylation-transalkylation system can also supply the hydrogen-containing material as recycled hydrogen from light gas processing to the dealkylation stage. The hydrogen concentration in the hydrogen-containing material can be of a refined quality (+99.9% mole purity) or it can be lower as part of a blended material. The other gases that comprise the hydrogen-containing material should be inert to the dealkylation process and not cause any side reactions, including such reactions that cause coking or deactivation of the hydrodealkylation catalyst. Preferably, the amount of non-hydrogen in the hydrogen-containing material should be minimized to reduce the size of processing equipment and to lower the consumption of energy. An embodiment of the method of forming mixed xylenes from a heavy reformate includes introducing the hydrogen-containing material where the hydrogen comprises at least about 99.9 mole percent of the material.

Process Reactions

The two main reactions of the dealkylation-transalkylation method are a dealkylation reaction, which uses hydrodealkylation to convert MEBs into toluene and benzene, and a transalkylation reaction, which converts toluene and benzenes with TMBs into toluene and mixed xylenes.

Dealkylation Reaction

The dealkylation reactions remove attached alkyl constituents from an aromatic base. Hydrodealkylation, a form of dealkylation, uses a combination of hydrogen and the presence of a dealkylation catalyst to free alkyl moieties and create alkanes through hydrogen saturation while maintaining the unsaturation of the base aromatic. For example, Equation 1 shows hydrogen and 1-methyl 3-ethyl benzene ("1M3EB", a MEB) forming toluene and ethane through the hydrodealkylation process:

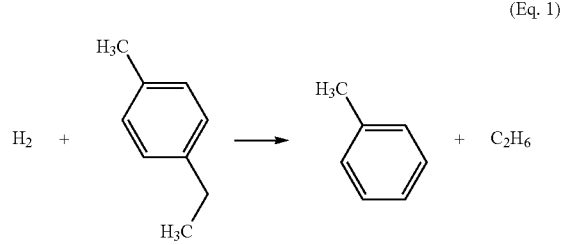

(Eq. 1)

The more carbons that are present on the alkyl constituency, the more likely the alkyl constituent is subject to dealkylation through hydrodealkylation. Non-MEB alkyl aromatics are capable of dealkylation in the presence of the hydrogen and the hydrodealkylation catalyst. Hydrodealkylation of n- and iso-propyl benzenes (nPB and iPB) can form combinations of ethane/toluene and propane/toluene reaction products. Hydrodealkylated n-butyl benzenes (nBB) tend to form butane/toluene reaction products—the n-butane does not schism into smaller alkane products in the presence of hydrogen. The formation of light olefins during hydrodealkylation occurs in small amounts. Methyl moieties, are orders of magnitude less reactive than the C2+ alkyl groups; however, with excess hydrogen, prolonged residence time and elevated temperature demethylization can occur. Therefore, the dealkylation stage is operated such that demethylization is mitigated.

For the hydrodealkylation reaction, a suitable dealkylation catalyst is selected by one of ordinary skill in the art that maximizes the dealkylation reaction of MEBs at the operating conditions of the dealkylation stage. Useful dealkylation catalysts include metal-loaded ZSM-5 or ZSM-12 zeolites. Another catalyst that is useful for dealkylation is the catalyst described in co-pending U.S. Provisional Patent Application No. 60/619,161 to Ercan, et al.

Transalkylation Reaction

The transalkylation reaction transfers an alkyl branch from one alkyl aromatic compound and attaches it to another aromatic or alkyl aromatic compound in exchange for a hydrogen atom. For example, Equation 2 shows 1,2,4 tri-methyl benzene ("124TMB", one of the TMBs) reacting with toluene to form two molecules of any of the three isomers of xylene.

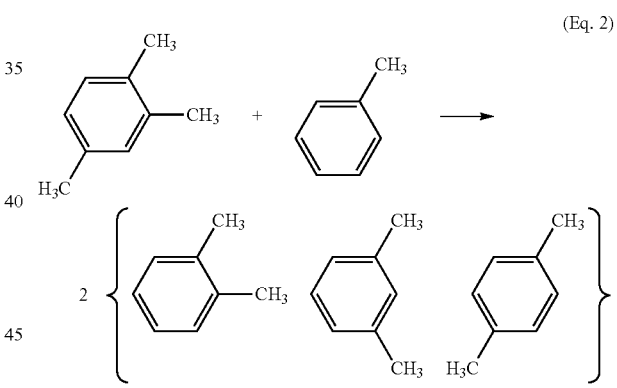

(Eq. 2)

The two xylene molecules formed in Equation 2 during any given transalkylation reaction do not have to be the same isomer of xylene. The reaction of Equation 2 and similar reactions produce amounts of all thee xylene isomers, resulting in the formation of mixed xylenes. For the reaction given in Equation 2, a number of factors influence the isomer distribution of the mixed xylenes, including the selection of the transalkylation catalyst and the isomer distribution of the TMBs. An embodiment of the method of forming mixed xylenes from the heavy reformate includes operating the transalkylation stage at conditions supporting maximization of paraxylene in the produced transalkylation stage product.

Other transalkylation reactions include disproportionation of two TMBs to form a xylene molecule and a C10 alkyl aromatic. Disproportionation reactions are not desirable as they foster deactivation of the transalkylation catalyst over time due to coking. Hydrogen, light alkanes and olefins can also form in small quantities during the transalkylation process.

For the transalkylation reaction, a suitable transalkylation catalyst is selected by one of ordinary skill in the art that maximizes the transalkylation reaction of TMBs to mixed xylenes at the operating conditions of the transalkylation stage. Useful transalkylation catalysts include ZSM-12, and beta or mordenite zeolites.

Optionally, a small amount of hydrogen, including hydrogen from the hydrogen-containing material, can be introduced as part of the overall transalkylation process to help facilitate the transalkylation reactions as well as prevent the formation of C10+ alkyl aromatics and polyaromatic precursors. The minor amount of hydrogen can quench reactive sites on the base aromatic if the alkyl transfer between two alkyl aromatic molecules is not successful.

Method of Forming Mixed Xylenes

The heavy reformate dealkylation-transalkylation method for creating mixed xylenes includes introducing into a dealkylation stage of the dealkylation-transalkylation system a heavy reformate and hydrogen-containing material. The heavy reformate and the hydrogen are introduced such that the MEBs and the hydrogen contact the hydrodealkylation catalyst contained in the dealkylation stage. An embodiment of the method of forming mixed xylenes includes where the feed ratio of hydrogen-containing material to heavy reformate is in a range of from about 1 to about 4.

An embodiment of the method of forming mixed xylenes from a heavy reformate includes introducing the heavy reformate and the hydrogen-containing material as separate fluid streams into the dealkylation stage. "Fluids" means vapors, liquids, gases and their combinations at their present condition. Combining heavy reformate and the hydrogen-containing material before introduction into the dealkylation stage intermingles the materials before contacting the hydrodealkylation catalyst.

The heavy reformate and the hydrogen-containing material contacts the hydrodealkylation catalyst in the dealkylation stage. The catalyst is operable to convert at least a significant portion if not all of the MEBs in the heavy reformate into toluene and ethane at the dealkylation stage operating conditions. One of ordinary skill in the art is capable of selecting an appropriate, commercially available hydrodealkylation catalyst for performing the dealkylation portion of the process without undue or excessive experimentation. Such parameters in selecting the physical, selectivity and activity attributes of an appropriate hydrodealkylation catalyst include dealkylation stage operating conditions, feed stock compositions, ratios of hydrogen to MEBs, desired conversion efficacy and efficiency, average dealkylation stage residence time and physical attributes of the vessel of the dealkylation stage.

The dealkylation stage operates such that toluene and non-aromatic gases form as products of the selective hydrodealkylation of MEBs while the TMBs are maintained and relatively unaffected. The reactions that occur during hydrodealkylation are similar to the reaction presented in Equation 1. An embodiment of the method of forming mixed xylenes from a heavy reformate includes operating the dealkylation stage such that the temperature is maintained in a range of from about 200° C. to about 540° C. An embodiment of the method includes maintaining the pressure of the dealkylation stage is in a range of from about 10 bars to about 50 bars. An embodiment of the method includes maintaining the fluid hourly space velocity (FHSV) for the dealkylation stage is in a range of from about 1 $hr^{-1}$ to about 5 $hr^{-1}$. An embodiment of the method includes introducing the hydrogen-containing material and the heavy reformate such that the feed ratio is in a range of from about 1 to about 4.

The dealkylation stage product includes toluene and TMBs. The dealkylation stage product can also include benzene and mixed xylenes from the dealkylation reaction as side-products. A useful dealkylation stage product includes toluene in a range of from about 10 wt. % to about 45 wt. % and TMBs in a range of from about 15 wt. % to about 70 wt. %. Other components are optionally present in the useful dealkylation stage product, including MEBs in a range of from 0 wt. % to about 15 wt. %; benzene in a range of from 0 wt. % to about 5 wt. %; light alkane gases, which are C1-5 gases, in the range of from 0 wt. % to about 25 wt. %; and light olefins in a range of from 0 wt. % to about 2 wt. %.

The method of dealkylation-transalkylation includes operating the non-aromatic product gas separations stage such that the non-aromatic gases formed during the dealkylation stage separate from the dealkylation stage product, forming not only the non-aromatic product gas but also the dealkylated heavy reformate. The dealkylated heavy reformate forms before introduction into the transalkylation stage. The selective separation of the non-aromatic gases from the dealkylation stage product forms the dealkylated heavy reformate. The non-aromatic product gas contains a useful and recoverable amount of hydrogen. The non-aromatic product gas also includes alkanes and alkenes that can interfere with the transalkylation process. Removal of the non-aromatic gases improves the longevity and effectiveness of the transalkylation catalyst.

An embodiment of the dealkylation-transalkylation system includes where the non-aromatic product gas separations stage and the dealkylation stage are part of the same vessel. An embodiment of the method of forming mixed xylenes from a heavy reformate includes where the selective separation of non-aromatic product gases and the dealkylation of the heavy reformate occurs in the same vessel. In such a method and system, the non-aromatic gases pass through a separations means, which may include a separations membrane selective for non-aromatics or a condenser that is operable to induce phase change in aromatic compounds but not the non-aromatic compounds, including light alkenes, alkanes, inerts and hydrogen. In some other methods, a separations means selectively separates the dealkylation non-aromatic gases from the dealkylated heavy reformate outside the dealkylation stage.

The heavy aromatics dealkylation-transalkylation method includes introducing the dealkylated heavy reformate into the transalkylation stage. The dealkylated heavy reformate is introduced such that the toluene and the TMBs contact the transalkylation catalyst contained in the transalkylation stage.

Optionally, the introduction of supplemental benzene, toluene, mixed xylenes or refined meta-xylene, and combinations thereof, can alter the resultant mix of the transalkylation process. Transalkylation reactions similar to the reaction shown in Equation 2 break down C9+ alkyl aromatics, especially C10 alkyl aromatics, into useful C7-8 alkyl aromatics. Sources of C6-8 aromatics and alkyl aromatics include not only stand-alone internal or external storage and production facilities but also recycle streams from a post-dealkylation-transalkylation refining and separations systems, including aromatics and xylene separations systems. An embodiment of the method of forming mixed xylenes from a heavy reformate includes recycling at least a portion of the benzene selectively separated from a produced transalkylation stage product back into the transalkylation stage. An embodiment of the method includes recycling at least a portion, if not all, of the toluene selectively separated from the produced transalkylation stage product back into the transalkylation stage. An embodiment of the method includes recycling at least a portion, if not all, of the mixed xylenes selectively separated from the produced transalkylation stage product back into the transalkylation stage. An embodiment of the method includes recycling at least a portion, if not all, of the meta-xylene selectively separated from the mixed xylenes back into the transalkylation stage. The recycled C6-8 aromatics and alkyl aromatics can form an intimate mixture with the dealkylated heavy reformate before introduction into the transalkylation stage or can be separately introduced into the transalkylation stage, or both if more than one stream is recycled.

The toluene and the TMBs in the dealkylated heavy reformate contact the transalkylation catalyst. The transalkylation catalyst is operable to convert a significant portion if not all of the TMBs in the dealkylated heavy reformate into mixed xylenes at the transalkylation stage operating conditions. One of ordinary skill in the art is capable of selecting an appropriate, commercially available transalkylation catalyst for performing the transalkylation portion of the process without undue or excessive experimentation. Such parameters include the physical, selectivity and activity attributes of an appropriate transalkylation catalyst include transalkylation operating conditions, feed stock compositions, ratios of toluene to TMBs, desired conversion efficacy and efficiency, stage residence time, and physical attributes of the second stage reaction vessel.

The configuration of the transalkylation stage can take one of several forms. An embodiment of the dealkylation-transalkylation system includes where the transalkylation stage is a fluidized catalyst bed. An embodiment of the dealkylation-transalkylation system includes where the transalkylation stage is a moving catalyst bed. In such configuration, the transalkylation catalyst can be removed, regenerated external to the transalkylation stage and reintroduced using processes known in the art similar to fluid catalytic cracking (FCC) and continuous catalytic reformer (CCR) systems. In such a system configuration, the optional hydrogen would not be used as the transalkylation catalyst would be continually regenerated and reintroduced.

The transalkylation stage operates such that a transalkylation stage product mixture forms from the selective transalkylation reaction. The reactions that occur during transalkylation are similar to the reaction presented in Equation 2. An embodiment of the method of forming mixed xylenes from a heavy reformate includes maintaining the temperature of the transalkylation stage in a range of from about 200° C. to about 540° C. An embodiment of the method includes maintaining the pressure of the transalkylation stage in a range of from about 10 bars to about 50 bars. An embodiment of the method includes maintaining the fluid hourly space velocity (FHSV) for the transalkylation stage is in a range of from about 1 hr$^{-1}$ to about 5 hr$^{-1}$.

The transalkylation stage product includes mixed xylenes. The transalkylation stage product can also include benzene, toluene, light gases, which can include alkanes, olefins or both, and unreacted MEBs and TMBs. A useful transalkylation stage product includes mixed xylenes in a range of from about 20 wt. % to about 40 wt. %. Other components that are optionally present include benzene in a range of from 0 wt. % to about 5 wt. %; toluene in a range of from 0 wt. % to about 30 wt. %; light gases in the range of from 0 wt. % to about 10 wt. %; MEBs in a range of from 0 wt. % to about 15 wt. %; TMBs in a range of from 0 wt. % to about 40 wt. %; and ethylbenzene in a range of from 0 wt. % to about 3 wt. %.

In an embodiment of the method of forming mixed xylenes from a heavy reformate, the transalkylation stage operates to selectively remove non-aromatic gases that form in the transalkylation stage reaction before passing the transalkylation stage product. Transalkylation stage non-aromatic gases can include hydrogen, light alkanes and some light olefins, which are the result of partially completed transalkylation and disassociation reactions.

The transalkylation stage feeds the transalkylation stage product into a post-dealkylation-transalkylation refining or separations system that is operable to separate most of the products in the transalkylation stage product mixture from one another. An embodiment of the method of forming mixed xylenes from a heavy reformate includes operating the dealkylation-transalkylation system such that benzene, toluene and mixed xylenes are selectively separated from the produced transalkylation stage product. The post-dealkylation-transalkylation refining system is operable to selectively separate the transalkylation stage product into several useful products, including non-aromatic gases, benzene, toluene and mixed xylenes. The remaining C9+ alkyl aromatics, which are the "bottoms" of the separated transalkylation stage product mixture, are conveyed into a separate fluid stream for other processing. As previously described, in some embodiments the dealkylation-transalkylation system is operable to convey at least a portion, if not all, of the benzene production, the toluene production or the mixed xylene production upstream to the transalkylation stage, or combinations thereof.

After separation, the remaining C9+ alkyl aromatics not previously eliminated are optionally recycled or stored for later, batch-like processing. An embodiment of the dealkylation-transalkylation system includes a recycle loop that fluidly couples the dealkylation stage to the post-dealkylation-transalkylation refining system and that is operable to convey C9+ alkyl aromatics recovered from the post-dealkylation-transalkylation refining system to the dealkylation stage. The unconverted or partially converted C9+ alkyl aromatics are conveyed to the upstream portion of the embodiment of the system and reintroduced directly into the dealkylation stage as a feedstock or blended with fresh heavy reformate feed. The recycle effectively results in a "recycle until extinction" for any introduced C9+ alkyl aromatics. This eliminates a potential waste stream and effectively converts all of the C9+ alkyl aromatics into useful components ranging from hydrogen to mixed xylenes.

The post-dealkylation-transalkylation refining system can further separate the xylene isomers into commercial-grade products or products for use as industrial feedstocks. An embodiment of the method of forming mixed xylenes from a heavy reformate includes operating the dealkylation-transalkylation system such that ortho-xylene, para-xylene and meta-xylene are selectively separated from the previously produced mixed xylenes. The individual xylene isomers are useful as products and as recycle feedstocks. As previously described, in some embodiments the dealkylation-transalkylation system is operable to convey at least a portion, if not all, of the meta-xylene production upstream to the transalkylation stage.

A gas separations system can selectively extract hydrogen from the light gas streams produced by the dealkylation and transalkylation stages. The gas handling system is operable to recover hydrogen from the dealkylation non-aromatic gases and the post-dealkylation-transalkylation refining and separations systems. Excess hydrogen can be recycled to the dealkylation stage for use in the hydrodealkylation reaction. An embodiment of the dealkylation-transalkylation system includes a recycle loop that fluidly couples the dealkylation stage to the non-aromatic product gas separations stage and that is operable to convey hydrogen recovered from the non-aromatic gases to the dealkylation stage. The gas separations system can direct the remaining gases from the process—light alkanes, alkenes and methane—towards other chemical or petrochemical processes outsides of the dealkylation-transalkylation system.

Supporting Equipment

Embodiments include many additional standard components or equipment that enables and makes operable the described apparatus, process, method and system. Examples of such standard equipment known to one of ordinary skill in the art includes heat exchanges, pumps, blowers, reboilers, steam generation, condensate handling, membranes, single and multi-stage compressors, separation and fractionation equipment, valves, switches, controllers and pressure-, temperature-, level and flow-sensing devices.

Operation, control and performance of portions of or entire steps of a process or method can occur through human interaction, pre-programmed computer control and response systems, or combinations thereof.

What is claimed is:

1. A method of forming mixed xylenes from a heavy reformate using a dealkylation-transalkylation system, the method comprising the steps of:
   introducing both the heavy reformate and a hydrogen-containing material into a dealkylation stage of the dealkylation-transalkylation system such that the heavy reformate and the hydrogen-containing material intermingle and contact a hydrodealkylation catalyst, where the dealkylation stage contains the hydrodealkylation catalyst, where the heavy reformate comprises a significant amount of both methyl ethyl benzenes and tri-methyl benzenes and is substantially free of toluene by weight, and where the hydrogen-containing material comprises hydrogen;
   operating the dealkylation stage such that toluene forms from the reaction methyl ethyl benzenes and hydrogen in the presence of the hydrodealkylation catalyst and such that a dealkylation stage product is produced, where the dealkylation stage product comprises toluene, tri-methyl benzenes and non-aromatic product gas;
   operating the non-aromatic product gas separations stage such that the non-aromatic product gas and a dealkylation heavy reformate are produced separately and the non-aromatic product gas from the dealkylation stage product is removed before it is introduced into the vessel where transalkylation occurs, where the dealkylation heavy reformate comprises toluene and tri-methyl benzenes;
   introducing the dealkylated heavy reformate into the transalkylation stage such that the dealkylated heavy reformate contacts a transalkylation catalyst, where the transalkylation stage contains the transalkylation catalyst; and
   operating the transalkylation stage such that mixed xylenes form from reaction of tri-methyl benzenes and toluene in the presence of the transalkylation catalyst and such that a transalkylation stage product is produced, where the transalkylation stage product mixture comprises xylenes.

2. The method of claim 1 where methyl ethyl benzenes comprise at least about 30 percent by weight of the introduced heavy reformate.

3. The method of claim 1 where a weight ratio value of methyl ethyl benzenes to tri-methyl benzenes in the introduced heavy reformate is in a range of from about 0.1 to about 3.

4. The method of claim 1 where the introduced heavy reformate comprises less than a detectable amount of toluene by weight.

5. The method of claim 1 where a feed ratio of hydrogen-containing material to heavy reformate is in a range of from about 1 to about 4.

6. The method of claim 1 where the selective separation non-aromatic product gases by a non-aromatic gas separator and the dealkylation of the heavy reformate occurs in a dealkylation reactor.

7. The method of claim 1 where the transalkylation stage operates at a temperature range of from about 200° C. to about 540° C., a pressure range of from about 10 bars to about 50 bars and a liquid hourly space velocity range of from about 1 $hr^{-1}$ to about 5 $hr^{-1}$.

8. The method of claim 1 further comprising the stop of operating the dealkylation-transalkylation system such that benzene, toluene and mixed xylenes are selectively separated from the produced transalkylation stage product.

9. The method of claim 8 further comprising the step of recycling at least a portion of the selectively separated benzenes into the transalkylation stage.

10. The method of claim 8 further comprising the step of recycling at least a portion of the selectively separated toluene into the transalkylation stage.

11. The method of claim 8 further comprising the step of recycling at least a portion of the selectively separated mixed xylenes into the transalkylation stage.

12. The method of claim 8 further comprising the step of operating The dealkylation-transalkylation system such that ortho-xylene, para-xylene and meta-xylene are selectively separated from the mixed xylenes.

13. The method of claim 12 further comprising the step of recycling at least a portion of the selectively separated meta-xylene into the transalkylation stage.

* * * * *

UNITED STATES PATENT AND TRADEMARK OFFICE
CERTIFICATE OF CORRECTION

Page 1 of 1

PATENT NO.         : 9,000,247 B2
APPLICATION NO.    : 13/866559
DATED              : April 7, 2015
INVENTOR(S)        : Raed Abudawoud It is certified that error appears in the above-identified patent and that said Letters Patent is hereby corrected as shown below:

In the Claims,

In Column 15, Line 37, Claim 1, the phrase "reaction methyl" should read --reaction of methyl--.

In Column 16, Line 31, Claim 8, the second to last word appears as "stop" and should read --step--.

In Column 16, Line 45, Claim 12, the second word appears as "The" and should read --the--.

Signed and Sealed this
First Day of September, 2015

Michelle K. Lee
*Director of the United States Patent and Trademark Office*